(12) United States Patent
Son et al.

(10) Patent No.: US 9,867,772 B2
(45) Date of Patent: Jan. 16, 2018

(54) COSMETIC COMPOSITION FOR IMPROVING SKIN ELASTICITY

(71) Applicants: Eui Dong Son, Yongin-si (KR); Dae Jin Min, Seoul (KR); Hui Kyoung Chang, Yongin-si (KR); Hyun Jung Choi, Suwon-si (KR); Seong A Cho, Seoul (KR); Ji Hyun Kim, Yongin-si (KR); Tae Ryong Lee, Yongin-si (KR)

(72) Inventors: Eui Dong Son, Yongin-si (KR); Dae Jin Min, Seoul (KR); Hui Kyoung Chang, Yongin-si (KR); Hyun Jung Choi, Suwon-si (KR); Seong A Cho, Seoul (KR); Ji Hyun Kim, Yongin-si (KR); Tae Ryong Lee, Yongin-si (KR)

(73) Assignee: AMOREPACIFIC CORPORATION, Seoul (KR)

( * ) Notice: Subject to any disclaimer, the term of this patent is extended or adjusted under 35 U.S.C. 154(b) by 389 days.

(21) Appl. No.: 14/506,128

(22) Filed: Oct. 3, 2014

(65) Prior Publication Data
US 2015/0044265 A1    Feb. 12, 2015

Related U.S. Application Data

(63) Continuation-in-part of application No. 13/819,763, filed as application No. PCT/KR2011/006405 on Aug. 30, 2011, now abandoned.

(30) Foreign Application Priority Data

Aug. 31, 2010    (KR) .................. 10-2010-0084506

(51) Int. Cl.
*A61K 36/185*    (2006.01)
*A61K 8/97*    (2017.01)
*A61K 8/64*    (2006.01)
*A61Q 19/08*    (2006.01)
*A61K 8/14*    (2006.01)
*A61K 36/18*    (2006.01)

(52) U.S. Cl.
CPC ............... *A61K 8/97* (2013.01); *A61K 8/14* (2013.01); *A61K 8/64* (2013.01); *A61K 36/18* (2013.01); *A61Q 19/08* (2013.01); *A61K 2800/56* (2013.01)

(58) Field of Classification Search
CPC . A61K 36/18; A61K 8/97; A61K 8/64; A61K 8/14; A61K 2800/56; A61Q 19/08
See application file for complete search history.

(56) References Cited

U.S. PATENT DOCUMENTS

2001/0016213 A1*  8/2001  Singh-Verma ........... A61K 8/97
                                                  424/725
2003/0180395 A1    9/2003  Bueter
2010/0098773 A1    4/2010  Hammer et al.
2010/0215726 A1    8/2010  Roth
2016/0287658 A1*  10/2016  Son ..................... A61K 36/899

FOREIGN PATENT DOCUMENTS

| CN | 101536967 | 9/2009 |
| JP | 08012566 A | 1/1996 |
| JP | 2006062991 A | 3/2006 |
| KR | 1020040059004 A | 7/2004 |
| KR | 1020100023372 A | 3/2010 |
| WO | 2009067095 | 5/2009 |
| WO | 2010032199 | 3/2010 |

OTHER PUBLICATIONS

Bharali, R., et al "Chemopreventive Action of Phyllanthus urinaria Linn on DMBA-induced Skin Carcinogenesis in Mice" Indian Journal of Experimental Biology, Nov. 2003,41, pp. 1325-1328.*
Step Communications, "New Peptide Prevents Photoaginng" Personal Care Magazine, Apr. 2, 2009, retrieved online from http://www.personalcaremagazine.com/story/4825/new-peptide-prevents-photoageing 5 pages.*
BBS Trends Com, Jan. 23, 2014, p. 1, http://bbs.trends.com.cn/forum.php?mod=viewthread&tid=787052&page=0,.
Chinese Office Action—CN Application No. 201180041870.8 dated Jan. 17, 2014 from the Chinese Patent Office.
Eugenio Revilla et al., "Comparison of Several Procedures Used for the Extraction of Anthocynains From Red Grapes", J. Agric. Food Chem., vol. 46, 1998, pp. 4592-4597.
H.B. MacPhillamy, "Drugs From Plants; Plant Science Bulletin", Botanical Society of America, vol. 9, No. 2, Apr. 1963, pp. 1-15.
Ilya Raskin et al., "Can an Apple a Day Keep the Doctor Away?", Current Pharmaceutical Design, vol. 10, 2004, pp. 3419-3429.
International Search Report with English Translation for International Application No. PCT/KR2011/006405 dated Apr. 27, 2012.
J. David Phillipson, "New Drugs From Nature—It Could Be Yew", Phytotherapy Research, vol. 13, 1999, pp. 2-8.
Ru-Yi Zhang et al., "The effect of complex prescription capsule of Shenwu on skin aging in the rats," Chinese Journal of Gerontology, 2007, vol. 27, No. 20, pp. 1964-1966.
Written Opinion for International Application No. PCT/KR2011/006405 dated Apr. 27, 2012.
Extended European Search Report—European Application No. 11822113.4 dated May 11, 2016, citing US20100215726 and WO2010032199, 7 pages.

* cited by examiner

Primary Examiner — Chris R Tate
Assistant Examiner — Aaron J Kosar
(74) Attorney, Agent, or Firm — Cantor Colburn LLP

(57) ABSTRACT

Provided is a cosmetic composition for improving skin elasticity containing *Phyllanthus urinaria* extract and a polymersome in which an anti-aging peptide is stabilized as active ingredients. The cosmetic composition of the present disclosure is efficacious in improving skin wrinkles, restoring skin elasticity and increasing skin water content, and thus is effective for improving skin elasticity.

12 Claims, 9 Drawing Sheets

SEQUENCE LISTING

```
<160> NUMBER OF SEQ ID NOS: 2

<210> SEQ ID NO 1
<211> LENGTH: 20
<212> TYPE: DNA
<213> ORGANISM: Artificial Sequence
<220> FEATURE:
<223> OTHER INFORMATION: primer

<400> SEQUENCE: 1
ctgagtgatg caggcaccta                                           20

<210> SEQ ID NO 2
<211> LENGTH: 20
<212> TYPE: DNA
<213> ORGANISM: Artificial Sequence
<220> FEATURE:
<223> OTHER INFORMATION: primer

<400> SEQUENCE: 2
ctctctgggc tcacttggac                                           20
```

COSMETIC COMPOSITION FOR IMPROVING SKIN ELASTICITY

CROSS-REFERENCE TO RELATED APPLICATION

This application is a continuation-in-part of U.S. patent application Ser. No. 13/819,763, filed on Feb. 28, 2013, which is a national stage entry of PCT/KR2011/006405, filed on Aug. 30, 2011, which claims priority to Korean Patent Application No. 10-2010-0084506, filed on Aug. 30, 2011, and all the benefits accruing therefrom under 35 U.S.C. §119, the contents of which in their entirety are herein incorporated by reference.

BACKGROUND

1. Field

The present disclosure relates to a cosmetic composition for improving skin elasticity.

2. Description of the Related Art

Structural changes of the epidermis, dermis, etc. due to aging result in reduced elasticity and drooping of the skin. The thickness of the dermis decreases gradually with aging. The total collagen content in the dermis decreases by 1% in a year after being adults and the remaining collagen fibers become gradually thicker, leading to increased crosslinking and decreased solubility, extensibility, etc. In addition, with aging, the proliferative activity of fibroblasts in the dermis decreases whereas the collagen synthesizing ability decreases and the collagen degradation rate increases. As a result, as the regeneration of the epidermis, dermis, etc. becomes slow and the adhesion between the epidermis and the dermis becomes weak, the skin elasticity is decreased rapidly.

SUMMARY

The present disclosure is directed to providing a cosmetic composition for improving skin elasticity, which is efficacious in improving skin wrinkles and restoring skin elasticity.

In one aspect, there is provided a cosmetic composition for improving skin elasticity, containing *Phyllanthus urinaria* extract and a polymersome in which one or more anti-aging peptide is enclosed and stabilized as active ingredients.

The cosmetic composition of the present disclosure is efficacious in improving skin wrinkles, restoring skin elasticity and increasing skin water content owing to a synergic effect of a combination of the *Phyllanthus urinaria* extract and the anti-aging peptide, and thus is more effective for improving skin elasticity as compared to when the active ingredients are used independently.

BRIEF DESCRIPTION OF THE DRAWINGS

The above and other aspects, features and advantages of the disclosed exemplary embodiments will be more apparent from the following detailed description taken in conjunction with the accompanying drawings in which.

DETAILED DESCRIPTION

Exemplary embodiments now will be described more fully hereinafter with reference to the accompanying drawings, in which exemplary embodiments are shown.

In an aspect, the present disclosure provides a cosmetic composition for improving skin elasticity containing *Phyllanthus urinaria* and a polymersome in which one or more anti-aging peptide is enclosed and stabilized as active ingredients.

In the present disclosure, "*Phyllanthus urinaria*" refers to a herb species also called chamberbitter or gripeweed which usually grows in fields or grasslands. *Phyllanthus urinaria* is known to be effective in treating enteritis, dysentery, edema caused by infectious hepatitis and nephritis, urinary tract infection, brightening eyes, infantile malnutrition, acute inflammation of eyes or corneal opacity, mouth ulcer, smallpox and occurrence of unknown furunculus in body and to provide a skin-whitening effect when included in cosmetics.

In the present disclosure, the *Phyllanthus urinaria* extract may be prepared according to methods well known in the art. For example, it may be extracted using water or an organic solvent, specifically, one or more selected from a group consisting of ethanol, methanol, butanol, ether, ethyl acetate and chloroform.

In the present disclosure, the "anti-aging peptide" may be any peptide exhibiting an effect of delaying skin aging known in the art, without limitation. For example, the anti-aging peptide may be diaminopropionoyl tripeptide-33, although not being limited thereto.

In the present disclosure, the diaminopropionoyl tripeptide-33 refers to a peptide derivative which improves skin transparency by removing carbonyl proteins formed in the horny layer of skin due to aging, stress, external harmful factors, etc. and may be synthesized from peptides having desired structures through peptide bonding of proteins according to methods well known in the art. In the present disclosure, the tripeptide may be specifically alanine-histidine-proline, but is not limited thereto.

Figure 1:
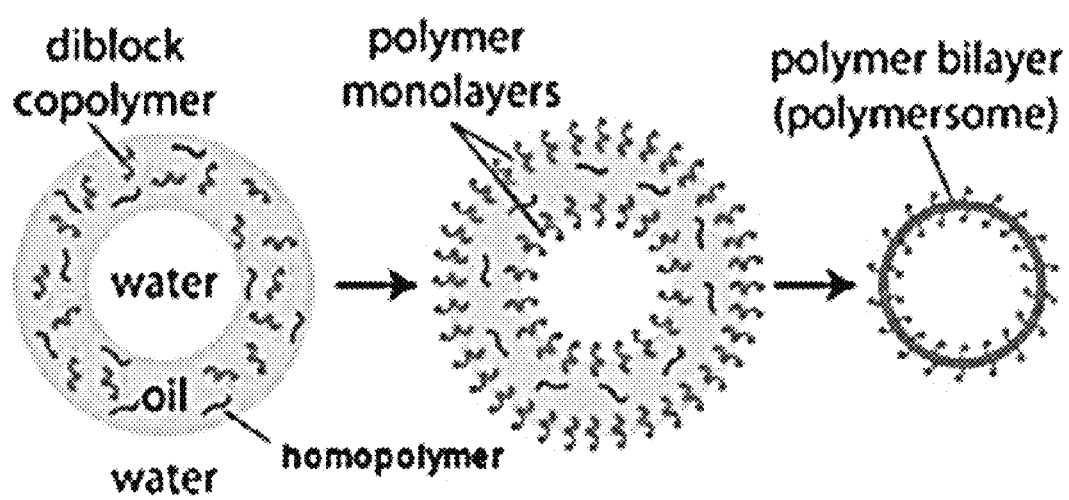
FIG. 1 shows an example of microfluidics technology.

In the present disclosure, the "polymersome" refers to an effective vesicle-type nanostructure synthesized from various amphiphilic polymers having both hydrophobic and hydrophilic blocks. In an aqueous solution, the amphiphilic polymers form aggregates according to the property of the hydrophilic blocks tending to aggregate together to decrease the free energy of the system. Since the hydrophilic blocks are uniformly dissolved in the aqueous solution, the polymersome may maintain a thermodynamically stable structure in the aqueous solution. The polymersome exhibits superior ability of penetrating into the skin and capturing active ingredients and is capable of maintaining the structure for a long period of time upon administration into the body because it is remarkably stable in aqueous solutions. Accordingly, since the peptide enclosed in the polymersome can remain without being adsorbed onto the membrane of the polymersome, the denaturation of peptide can be prevented and the efficacy of the peptide can be maintained. In the present disclosure, the polymersome may be synthesized by the microfluidics technology as shown in FIG. 1 (*J. Soc., Cosmet. Scientists Korea*, Vol. 34, No. 4, December 2008, 245-248), which is the cutting-edge technology capable of creating a new-concept tissue engineering structure of desired size, dimension and function by controlling the flow of a fluid. The polymersome is synthesized as a double inner layer structure. The innermost aqueous layer encloses the anti-aging peptide as the active ingredient and it is surrounded by a volatile solvent such as chloroform in which a copolymer is dissolved.

If the polymer is cured after removing the solvent, the active ingredient which has a molecular weight of 500 or greater cannot escape and is enclosed in the polymersome.

Specifically, the polymer used to prepare the polymersome may be a hydroxyethyl acrylate/sodium acryloyldimethyl taurate copolymer or an acrylate/stearyl methacrylate copolymer.

In the present disclosure, the polymersome is synthesized to have a particle diameter of 300-1,000 nm so that it can be absorbed through the skin. In the present disclosure, the peptide as the active ingredient may be enclosed in the polymersome either alone or in combination of two or more.

In the present disclosure, "enclosing" means that the peptide exists in the polymersome as separated from the membrane of the polymersome. As a result, the denaturation of peptide can be prevented and the efficacy of the peptide can be maintained.

In the present disclosure, the polymersome in which the anti-aging peptide is stabilized may be specifically ABCELL™.

In the cosmetic composition for improving skin elasticity according to the present disclosure, the anti-aging peptide may be diaminopropionoyl tripeptide-33.

In the cosmetic composition for improving skin elasticity according to the present disclosure, the polymersome may be contain 5-15 wt % of the anti-aging peptide based on the total weight of the polymersome. When the amount of the anti-aging peptide is in the above-described range, the anti-aging effect may be expected and the effect on the *Phyllanthus urinaria* extract as the other active ingredient may be not great. In this aspect, the polymersome may be contain 6-14 wt %, 7-13 wt %, 8-12 wt % or 9-11 wt % of the anti-aging peptide based on the total weight of the polymersome.

The composition of the present disclosure may increase expression of the perlecan gene and increase production of the perlecan protein. Perlecan is a proteoglycan existing in the epidermis and the dermis and has been found, with various growth factors attached thereto, to affect proliferation, differentiation and adhesion of epidermal cells. The composition of the present disclosure increases expression of the perlecan gene, thereby maintaining the skin structure by promoting regeneration of the epidermis and the dermis and the improvement of adhesion between the epidermis and the dermis. Accordingly, it may improve and restore skin elasticity.

Further, the composition restores production of the perlecan protein decreased by UV.

The composition of the present disclosure improves skin wrinkles, restores skin elasticity and increases skin water content.

The examples (and experiments) will now be described. The following examples (and experiments) are for illustrative purposes only and not intended to limit the scope of the present disclosure.

[Example 1] Preparation of *Phyllanthus urinaria* Extract 0.5 kg of dried *Phyllanthus urinaria* was added to 2 L of a 70% ethanol aqueous solution corresponding to 4 times based on weight. After extracting 3 times under reflux, the resulting extract was settled for 3 days. Then, after filtration through filter cloth and centrifugation, the filtrate was separated from the residue and the separated filtrate was concentrated under reduced pressure to obtain *Phyllanthus urinaria* extract.

[Example 2] Preparation of Polymersome in which Diaminopropionoyl Tripeptide-33 is Enclosed After dissolving the ingredients described in Table 1 in chloroform, a polymersome was synthesized using the microfluidics technology (*J. Soc., Cosmet. Scientists Korea*, Vol. 34, No. 4, December 2008, 245-248). Then, a polymersome in which diaminopropionoyl tripeptide-33 having an alanine-histidine-proline tripeptide structure is enclosed (hereinafter, ABCELL™.) was synthesized by removing chloroform and curing the polymersome.

TABLE 1

| Ingredients | Composition (%) |
|---|---|
| Water | Up to 100% |
| Hydroxyethyl acrylate/sodium acryloyldimethyl taurate copolymer | 0.50% |
| 1,2-Hexanediol | 0.50% |
| Methoxy PEG-114/poly(ε-caprolactone) | 0.50% |
| Hydrogenated phosphatidylcholine | 0.00175% |
| Cholesterol | 0.0006% |
| Acrylate/stearyl methacrylate copolymer | 0.000125% |
| Dextrin | 0.000625% |
| Diaminopropionoyl tripeptide-33 | 10% |

[Comparative Example 1] Preparation of Polymersome in which Diaminopropionoyl Tripeptide-33 is not Enclosed A polymersome in which diaminopropionoyl tripeptide-33 is not enclosed was prepared in the same manner as described in Example 2, except that among the ingredients described in Table 1 the ingredients excluding diaminopropionoyl tripeptide-33 was dissolved in chloroform.

[Test Example 1] Experiment for Increase of Perlecan Gene (Isolation of RNA and RT-PCR)

Fibroblasts obtained from a newborn infant were seeded onto a 60-mm cell culture dish using DMEM containing 10% serum at a density of $1.25 \times 10^6$ cells/dish and cultured at 37° C. in a 5% CO$_2$ incubator to about 80% confluency. After starvation for 24 hours, the cells were treated with *Phyllanthus urinaria* extract and ABCELL™ at various concentrations (when treated with both *Phyllanthus urinaria* extract and ABCELL™, they were treated at a ratio of 1:1), which had been washed twice with PBS, and cultured for 2 days. After removing the medium, RNA was isolated according to the Invitrogen's RNA separation method by adding 1 mL of Trizol (Invitrogen). After quantifying RNA at 260 nm using a UV detector (Hewlett Packard), reverse transcription-polymerase chain reaction (RT-PCR) was carried out. For genetic analysis of each sample, correction was made using the complementary 36B4 gene. The primer sequences of perlecan are as follows.

Sense: 5'-ctgagtgatgcaggcaccta-3' (SEQ ID NO: 1)
Antisense: 5'-ctctctgggctcacttggac-3' (SEQ ID NO: 2)

Figure 2:
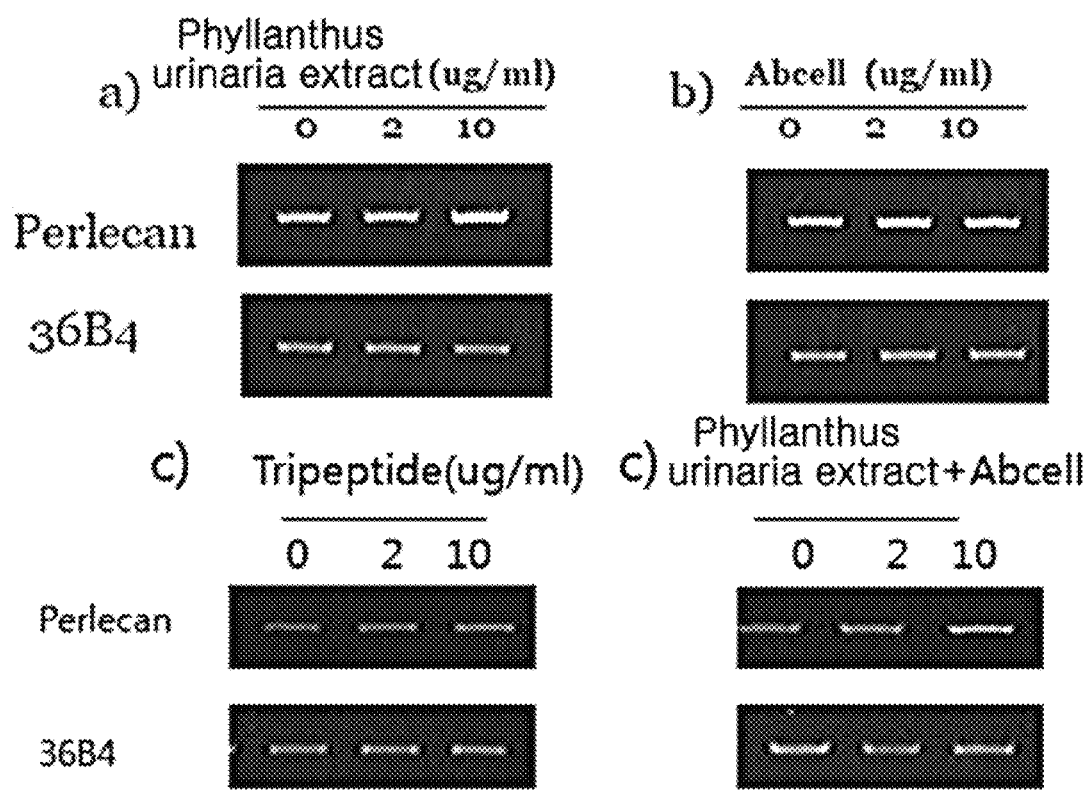
FIG. 2 shows change in the level of perlecan gene in normal human fibroblasts.

As seen from FIG. 2, *Phyllanthus urinaria* extract and ABCELL™ resulted in increased level of perlecan in the fibroblasts.

[Test Example 2] Change in Perlecan Using Immunofluorescence Staining

Normal human fibroblasts were seeded onto a 60-mm cell culture dish using DMEM containing 10% serum at a density of 1.25×10$^6$ cells/dish and cultured at 37° C. in a 5% CO$_2$ incubator to about 80% confluency. After starvation for 24 hours, the cells were washed twice with PBS and cultured for 2 days while irradiating UV B and treating with 10 μg/mL *Phyllanthus urinaria* extract or ABCELL™. Then, increasing situation of the perlecan protein in cell status was investigated.

Adult human dermal fibroblasts (HDFa) purchased from Cascade Biologics (USA) were cultured using M106 medium (Cascade Biologics, USA) at 37° C. in a 5% CO$_2$ incubator.

After spotting the cells onto a slide glass for immunofluorescence staining and treating with a substance for 48 hours, immunofluorescence staining was carried out. Details about the immunofluorescence staining are as follows. The cells were washed twice with DPBS and then fixed by treating with 3.5% paraformaldehyde for 10 minutes. The fixed cells were washed 3 times with DPBS, for 10 minutes each, and treated with 0.1% Triton X-100 for 5 minutes for permeation into the cells. After washing with PBS for 10 minutes, the cells were blocked with 5% goat serum for 30 minutes. After the blocking, the cells were treated with 5% goat serum with primary antibody added. Then, incubation was performed at room temperature for 1 hour so that the primary antibody (anti-perlecan antibody, Santa Cruz Biotechnology, USA) could bind to the corresponding antibody. After removing surplus primary antibody by washing 3 times with DPBS, for 10 minutes each, the cells were treated with secondary antibody at room temperature for 30 minutes. Surplus secondary antibody was completely removed by washing 3 times with DPBS, for 10 minutes each. After dropping one drop of a mounting solution onto a slide glass, followed by covering with a cover slip, the surplus mounting solution leaking out of the cover slip was removed and the cover slip was sealed.

Then, difference in fluorescence of each test group was observed using a confocal microscope.

Figure 3:
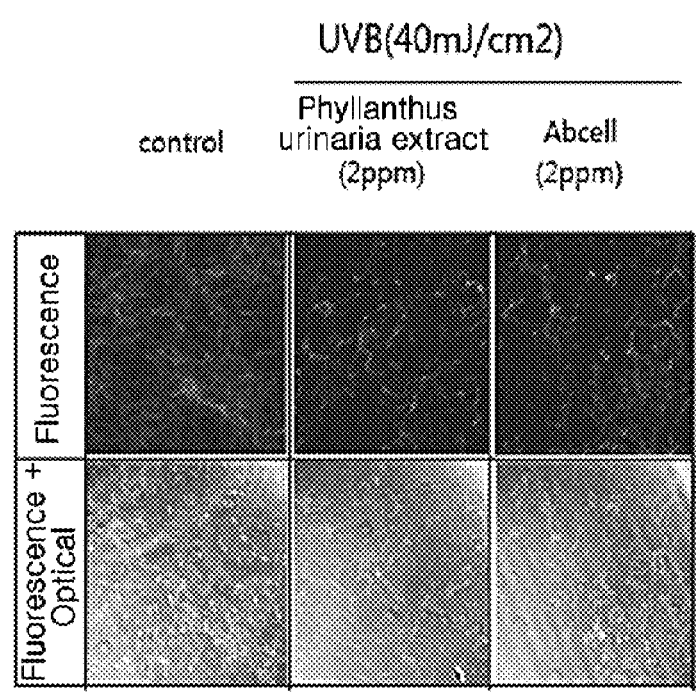
FIG. 3 shows change in the level of perlecan protein in normal human fibroblasts.

As a result, it was confirmed that UV B resulted in decrease of perlecan and the *Phyllanthus urinaria* extract or ABCELL™ restored the production of perlecan decreased by UV (FIG. 3).

[Test Example 3] Experiment for Restoration of Perlecan Level by ABCELL™

Normal human fibroblasts (NHFs; isolated from adults in 20 and 40 years old) were seeded onto a 60-mm cell culture dish using DMEM containing 10% serum at a density of 1.25×10$^6$ cells/dish and cultured at 37° C. in a 5% CO$_2$ incubator to about 80% confluency. The cultured cells were treated with 1% FBS medium+Cytokinol 100 ppm+10% BASF for 48 hours and observed after perlecan staining. ABCELL™ was treated at a concentration of 10 ug/mL. The procedure was similar to that of Test Example 4.

Figure 4:
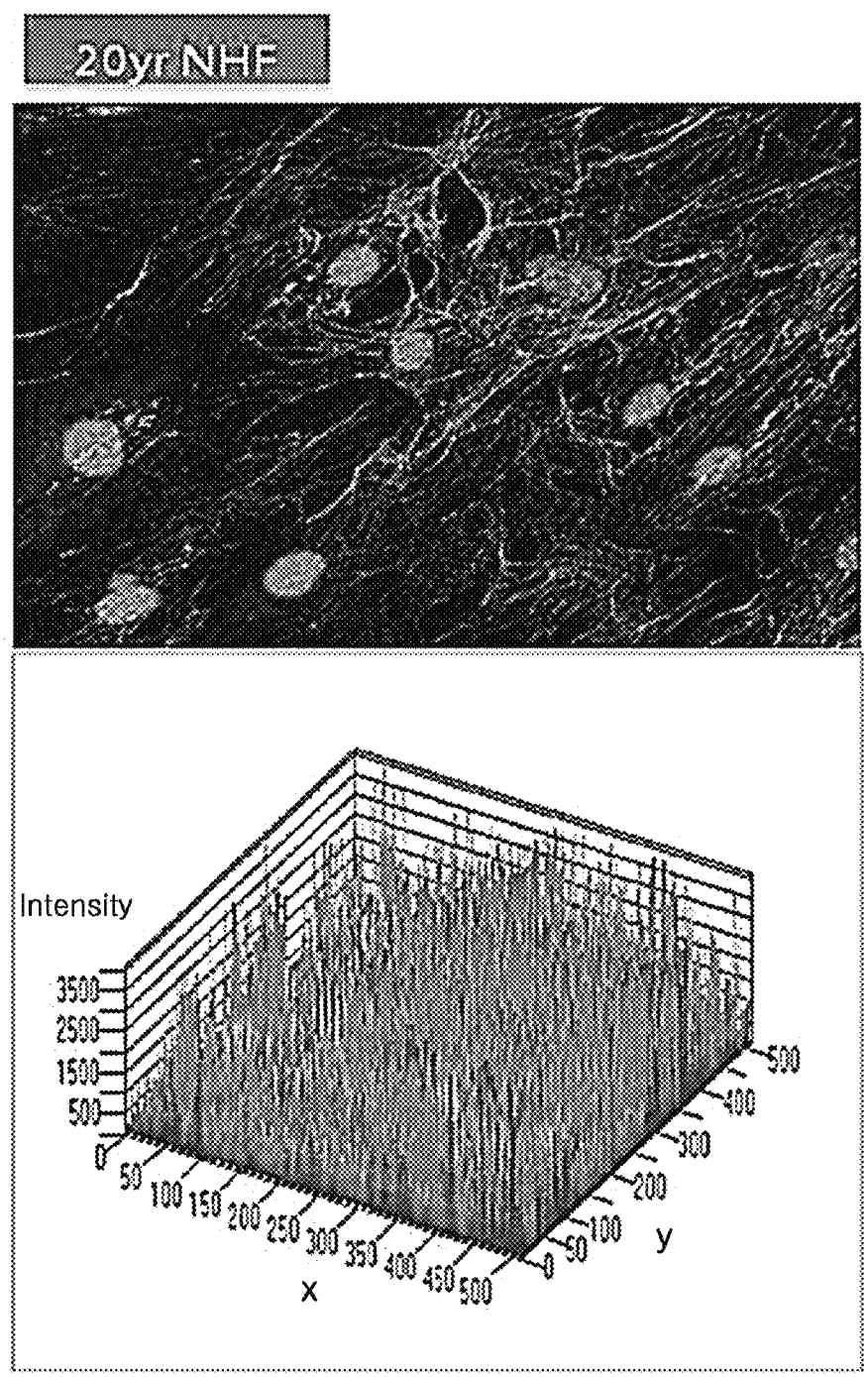
FIG. 4 shows change in perlecan protein isolated from normal human fibroblasts of an adult in his 20s as fluorescence intensity after immunofluorescence staining.
Figure 5:
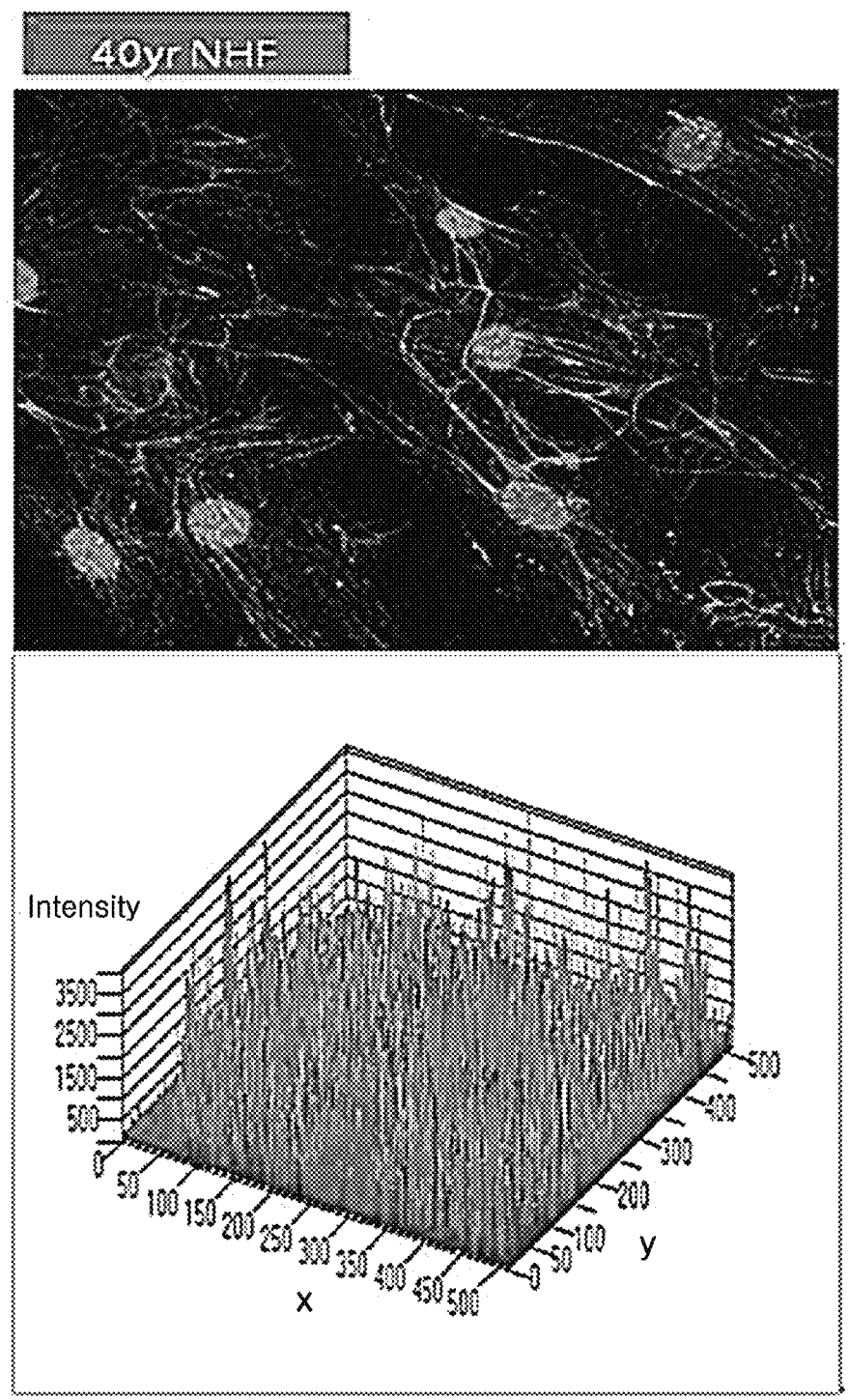
FIG. 5 shows change in perlecan protein isolated from normal human fibroblasts of an adult in his 40s as fluorescence intensity after immunofluorescence staining.
Figure 6:
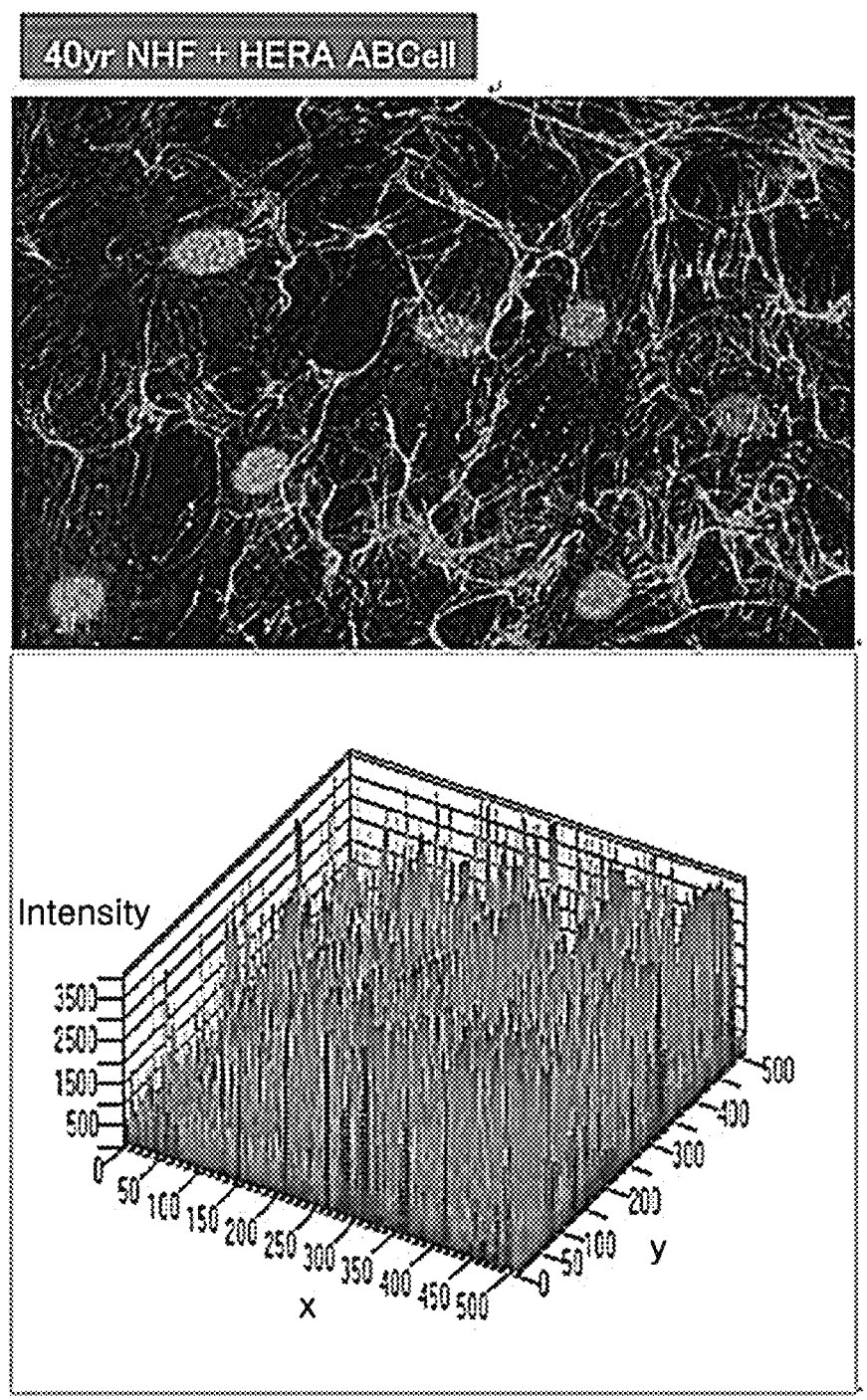
FIG. 6 shows change in perlecan protein isolated from normal human fibroblasts of an adult in his 40s as fluorescence intensity after immunofluorescence staining.

A result of measuring fluorescence intensity is shown in Table 2 and FIGS. 4-6. It was confirmed that the level of perlecan was decreased lower in the NHFs of the 40-year-old adult than in the NHFs of the 20-year-old adult (FIG. 4 and FIG. 5), and the decreased level of perlecan in the NHFs of the 40-year-old adult was restored to the level of the NHFs of the 20-year-old adult by HERA™ ABCELL™ (FIG. 5 and FIG. 6).

TABLE 2

|  | 20-yr NHF | 40-yr NHF | 40-yr NHF + ABCELL ™ |
|---|---|---|---|
| Intensity (Perlecan) | 756 | 544 | 937 |
| Relative value to 20-yr NHF | 100 | 72 | 124 |
| Relative value to 40-yr NHF | 139 | 100 | 172 |

[Test Example 4] Experiment for Increase of Elastin by ABCELL™

Normal human fibroblasts were seeded onto a 60-mm cell culture dish using DMEM containing 10% serum at a density of 1.25×10$^6$ cells/dish and cultured at 37° C. in a 5% CO$_2$ incubator to about 80% confluency. The cultured cells were treated with 0.2% *Phyllanthus urinaria* extract, 0.2% diaminopropionoyl tripeptide-33 (alanine-histidine-proline tripeptide), a mixture of 0.1% *Phyllanthus urinaria* extract and 0.1% diaminopropionoyl tripeptide-33 or a mixture of 0.1% *Phyllanthus urinaria* extract and 0.1% ABCELL™, per 100 mL of DMEM.

Figure 7:
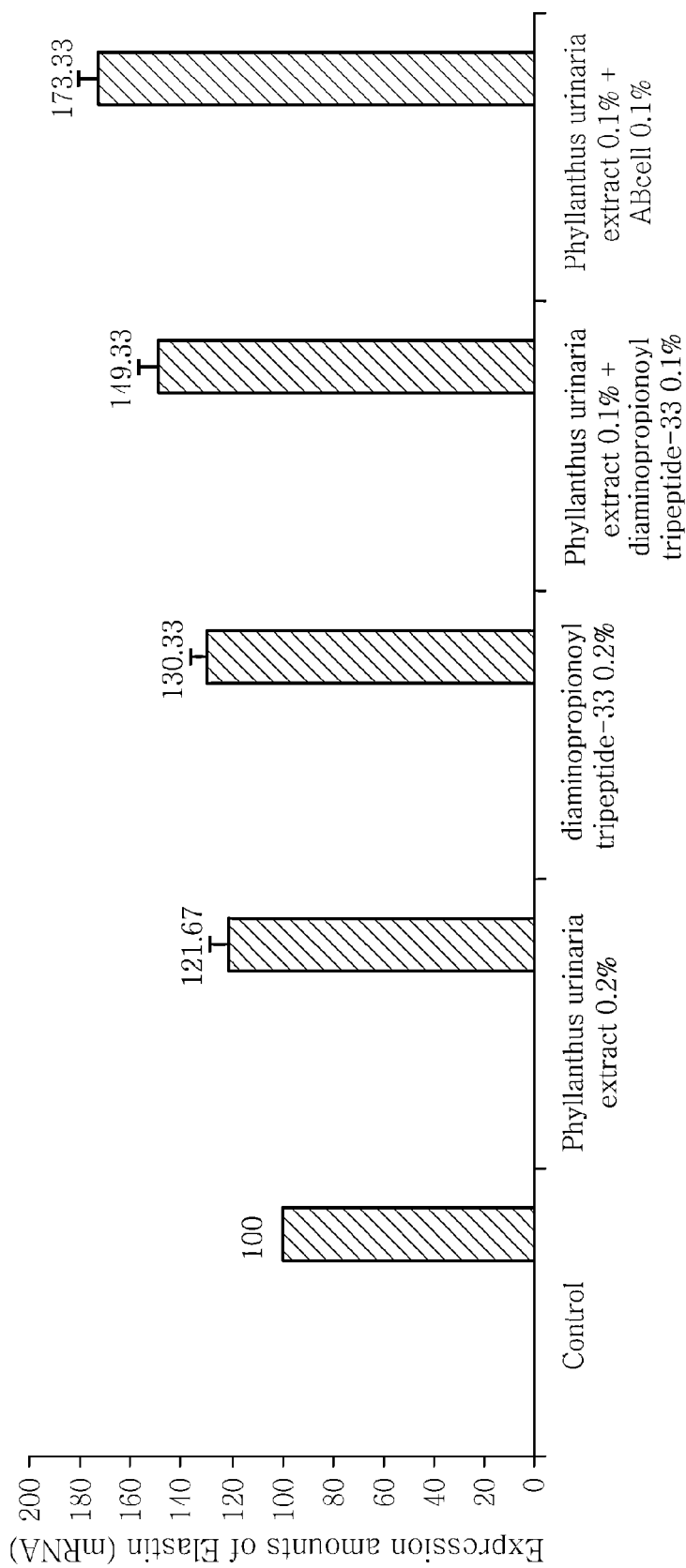
FIG. 7 shows an expression level of the elastin gene.

RNA was isolated from the cultured fibroblasts using Trizol and cDNA was synthesized using the Superscript reverse transcriptase III kit. Real-time PCR for genetic analysis was conducted using 2× TaqMan universal PCR mixture (10 μL), 20× TaqMan expression assay mix (1 μL), the cDNA (50 ng) and elastin primer (Hs00355783_m1*) using the 7500 Fast Real-Time PCR system. The expression level of the elastin gene (mRNA) of the control and test groups was compared relative to that of the 36B4 gene (control gene) in FIG. 7.

[Test Example 5] Improvement of Skin Wrinkles and Elasticity

A clinical trial was conducted by Dermapro (Seongnam, Korea), an independent clinical trial institute, for the effect of improving skin wrinkles and elasticity of a cosmetic formulation of Table 5 which contains *Phyllanthus urinaria* extract and ABCELL™. 40 women in their 30s and 40s were divided into two groups, 20 people each, and were asked to apply the formulation on the face twice a day, in the morning and evening, for 12 weeks. Then, improvement of skin wrinkles and elasticity were tested for 8 weeks using replicas according to arbitrary units (R1-R5).

Figure 8:
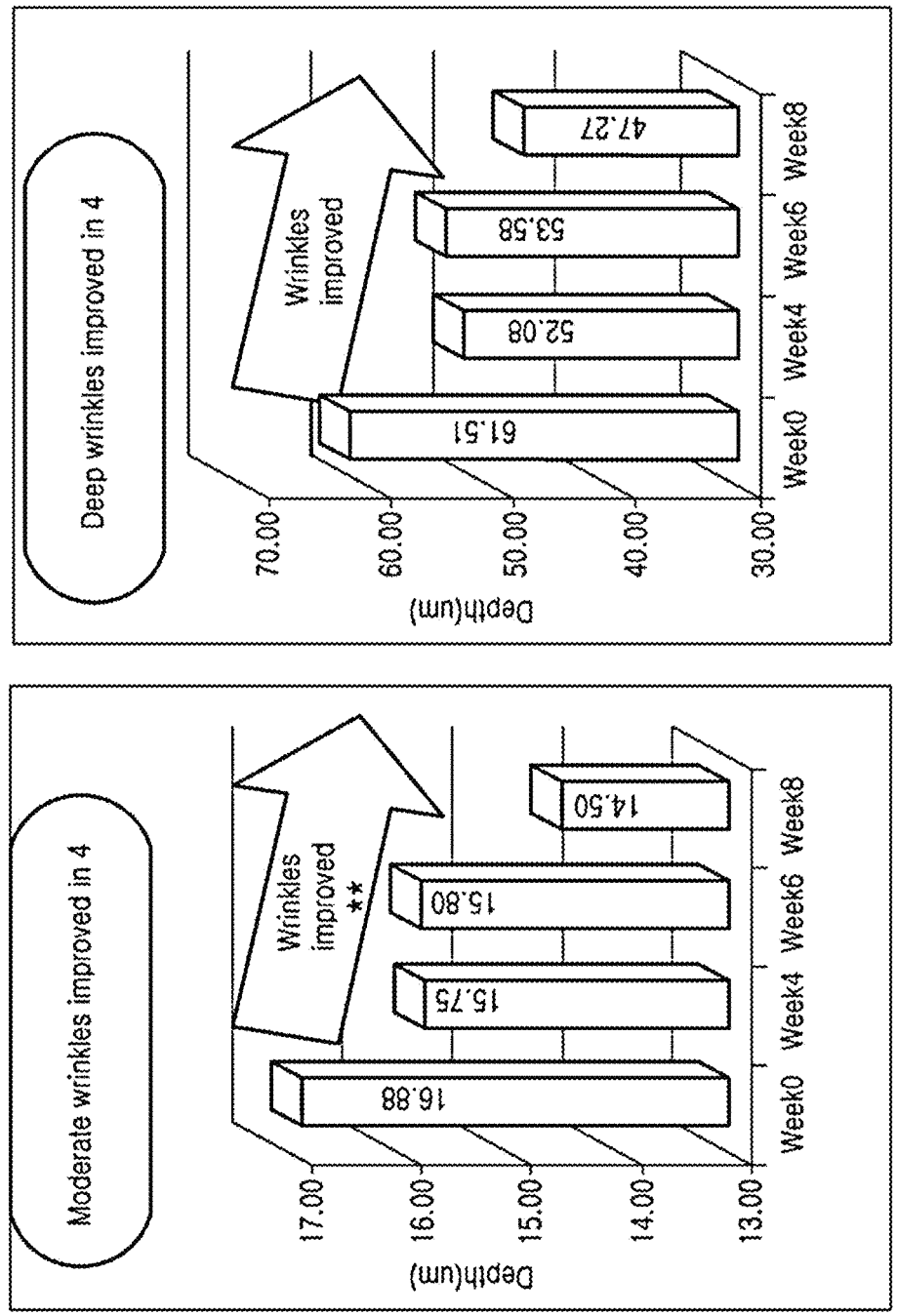
FIG. 8 shows a result of a clinical trial on skin wrinkles carried out by DERMAPRO Co., LTD., an independent clinical trial institute, for cosmetic formulations containing *Phyllanthus urinaria* extract and ABCELL™.
Figure 9:
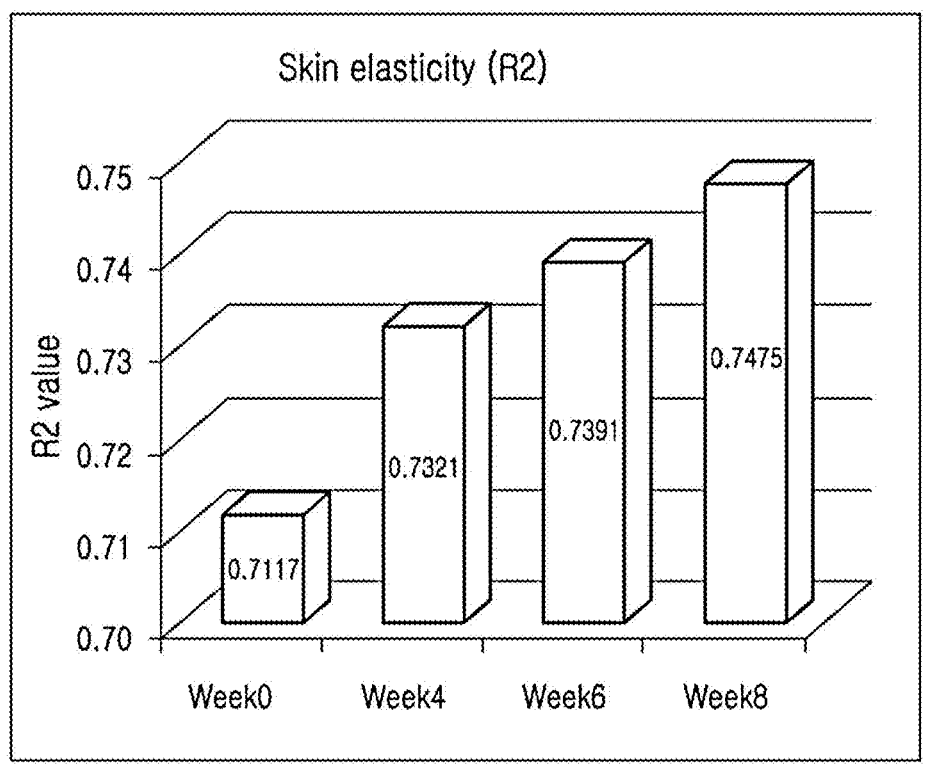
FIG. 9 shows a result of a clinical trial on the improvement of skin elasticity carried out by Dermapro for cosmetic formulations containing *Phyllanthus urinaria* extract and ABCELL™.

The effect of improving skin wrinkles and elasticity was observed from 4 weeks after the application of the formulation (FIG. 8 and FIG. 9).

[Test Example 6] Improvement of Skin Water Content

Skin moisturizing effect of the formulations described in Table 3 was evaluated as follows. 40 women in their 30s and 40s were divided into two groups, 20 people each, and were asked to apply the formulation on the face twice a day, in the morning and evening, for 12 weeks. Then, skin water content was measured using a corneometer (Germany). The result is given in Table 4.

As can be seen from Table 4, the skin water content increased rapidly with time owing to the synergic effect of *Phyllanthus urinaria* extract and ABCELL™.

Formulation examples of the cosmetic composition and the pharmaceutical composition according to the present disclosure are described below. However, the following examples are for illustrative purposes only and not intended to limit the scope of the present disclosure.

[Formulation Example 1] Softening Lotion (Skin Lotion)

A softening lotion was prepared according to a commonly employed method with the composition described in Table 5.

TABLE 3

| Ingredients | Comp. Ex. 2 | Comp. Ex. 3 | Comp. Ex. 4 | Comp. Ex. 5 | Comp. Ex. 6 | Ex. 3 |
|---|---|---|---|---|---|---|
| Purified water | balance | balance | balance | balance | balance | balance |
| *Phyllanthus urinaria* extract of Ex. 1 | — | 0.2 | — | — | — | 0.1 |
| Diaminopropionoyl tripeptide-33 | — | — | 0.2 | — | 0.1 | — |
| Polymersome not enclosing diaminopropionoyl tripeptide-33 of Comp. Ex. 1 | — | — | — | 0.2 | 0.1 | — |
| ABCELL ™ | — | — | — | — | — | 0.1 |
| Hydrogenated vegetable oil | 1.5 | 1.5 | 1.5 | 1.5 | 1.5 | 1.5 |
| Stearic acid | 0.6 | 0.6 | 0.6 | 0.6 | 0.6 | 0.6 |
| Glyceryl stearate | 1 | 1 | 1 | 1 | 1 | 1 |
| Stearyl alcohol | 2.5 | 2.5 | 2.5 | 2.5 | 2.5 | 2.5 |
| Polyglyceryl-10 pentastearate, behenyl alcohol & sodium stearoyl lactylate | 1 | 1 | 1 | 1 | 1 | 1 |
| Arachidyl behenyl alcohol & arachidyl glucoside | 1 | 1 | — | 1 | 1 | 1 |
| Cetearyl alcohol & cetearyl glucoside | 2 | 2 | 2 | 2 | 2 | 2 |
| PEG-100 stearate, glycerol oleate & propylene glycol | 1.5 | 1.5 | 1.5 | 1.5 | 1.5 | 1.5 |
| Caprylic/capric triglyceride | 11 | 11 | 11 | 11 | 11 | 11 |
| Cyclomethicone | 6 | 6 | 6 | 6 | 6 | 6 |
| Antiseptic, fragrance | adequate | adequate | adequate | adequate | adequate | adequate |
| Triethanolamine | 0.1 | 0.1 | 0.1 | 0.1 | 0.1 | 0.1 |

TABLE 4

| Test substance | Corneometer value | | |
|---|---|---|---|
| | Week 0 | Week 4 | Week 8 |
| Comparative Example 2 | 21 ± 4 | 23 ± 5 | 23 ± 3 |
| Comparative Example 3 | 21 ± 5 | 24 ± 5 | 25 ± 4 |
| Comparative Example 4 | 21 ± 6 | 24 ± 6 | 25 ± 6 |
| Comparative Example 5 | 20 ± 5 | 24 ± 5 | 25 ± 5 |
| Comparative Example 6 | 20 ± 9 | 24 ± 6 | 26 ± 6 |
| Example 3 | 20 ± 5 | 27 ± 6 | 33 ± 5 |

TABLE 5

| Ingredients | Contents (wt %) |
|---|---|
| *Phyllanthus urinaria* extract | 0.1 |
| ABCELL ™ | 0.1 |
| Glycerin | 3.5 |
| Oleyl alcohol | 1.5 |
| Ethanol | 5.5 |
| Polysorbate 80 | 3.2 |
| Carboxyvinyl polymer | 1.0 |

TABLE 5-continued

| Ingredients | Contents (wt %) |
|---|---|
| Butylene glycol | 2.0 |
| Propylene glycol | 2.0 |
| Antiseptic, fragrance | adequate |
| Purified water | balance |
| Total | 100 |

[Formulation Example 2] Nourishing Lotion (Milk Lotion)

A nourishing lotion was prepared according to a commonly employed method with the composition described in Table 6.

TABLE 6

| Ingredients | Contents (wt %) |
|---|---|
| *Phyllanthus urinaria* extract | 0.1 |
| ABCELL ™ | 0.1 |
| Glycerin | 3.0 |
| Butylene glycol | 3.0 |
| Propylene glycol | 3.0 |
| Carboxyvinyl polymer | 0.1 |
| Beeswax | 4.0 |
| Polysorbate 60 | 1.5 |
| Caprylic/capric triglyceride | 5.0 |
| Squalane | 5.0 |
| Sorbitan sesquioleate | 1.5 |
| Cetearyl alcohol | 1.0 |
| Triethanolamine | 0.2 |
| Antiseptic, fragrance | adequate |
| Purified water | balance |
| Total | 100 |

[Formulation Example 3] Nourishing Cream

A nourishing cream was prepared according to a commonly employed method with the composition described in Table 7.

TABLE 7

| Ingredients | Contents (wt %) |
|---|---|
| *Phyllanthus urinaria* extract | 0.1 |
| ABCELL ™ | 0.1 |
| Glycerin | 3.5 |
| Butylene glycol | 3.0 |
| Liquid paraffin | 7.0 |
| β-Glucan | 7.0 |
| Carbomer | 0.1 |
| Caprylic/capric triglyceride | 3.0 |
| Squalane | 5.0 |
| Cetearyl glucoside | 1.5 |
| Sorbitan stearate | 0.4 |
| Polysorbate 60 | 1.2 |
| Triethanolamine | 0.1 |
| Antiseptic, fragrance | adequate |
| Purified water | balance |
| Total | 100 |

[Formulation Example 4] Massage Cream

A massage cream was prepared according to a commonly employed method with the composition described in Table 8.

TABLE 8

| Ingredients | Contents (wt %) |
|---|---|
| *Phyllanthus urinaria* extract | 0.1 |
| ABCELL ™ | 0.1 |
| Glycerin | 8.0 |
| Butylene glycol | 3.0 |
| Liquid paraffin | 45.0 |
| β-Glucan | 7.0 |
| Carbomer | 0.1 |
| Caprylic/capric triglyceride | 3.0 |
| Beeswax | 4.0 |
| Cetearyl glucoside | 1.5 |
| Sorbitan sesquioleate | 0.9 |
| Paraffin | 1.5 |
| Antiseptic, pigment, fragrance | adequate |
| Purified water | balance |
| Total | 100 |

[Formulation Example 5] Pack

A pack was prepared according to a commonly employed method with the composition described in Table 9.

TABLE 9

| Ingredients | Contents (wt %) |
|---|---|
| *Phyllanthus urinaria* extract | 0.1 |
| ABCELL ™ | 0.1 |
| Glycerin | 4.0 |
| Polyvinyl alcohol | 15.0 |
| Hyaluronic acid extract | 5.0 |
| β-Glucan | 7.0 |
| Allantoin | 0.1 |
| Nonyl phenyl ether | 0.4 |
| Polysorbate 60 | 1.2 |
| Ethanol | adequate |
| Antiseptic, fragrance | adequate |
| Purified water | balance |
| Total | 100 |

[Formulation Example 6] Patch

A patch was prepared according to a commonly employed method with the composition described in Table 10.

TABLE 10

| Ingredients | Contents (wt %) |
|---|---|
| *Phyllanthus urinaria* extract | 0.1 |
| ABCELL ™ | 0.1 |
| β-1,3-Glucan | 3.0 |
| Diethylamine | 0.7 |
| Sodium sulfite | 0.1 |
| Polyoxyethylene lauryl ether (E.O = 9) | 1.0 |
| Polyhydroxyethylene cetyl stearyl ether (Cetomacrogol 1000) | 1.0 |
| Viscous paraffin oil | 2.5 |
| Caprylic/capric ester (Cetiol LC) | 2.5 |
| Polyethylene glycol 400 | 3.0 |
| Polyacrylic acid (Carbopol 934P) | 1.0 |
| Purified water | balance |
| Total | 100 |

While the exemplary embodiments have been shown and described, it will be understood by those skilled in the art that various changes in form and details may be made thereto without departing from the spirit and scope of the present disclosure as defined by the appended claims.

In addition, many modifications can be made to adapt a particular situation or material to the teachings of the present disclosure without departing from the essential scope thereof. Therefore, it is intended that the present disclosure not be limited to the particular exemplary embodiments disclosed as the best mode contemplated for carrying out the present disclosure, but that the present disclosure will include all embodiments falling within the scope of the appended claims.

What is claimed is:

1. A cosmetic composition for improving skin elasticity comprising effective amounts of:
    *Phyllanthus urinaria* extract; and
    a polymersome in which one or more anti-aging peptide is enclosed,
    as active ingredients,
    wherein the *Phyllanthus urinaria* extract is an ethanol extract of *Phyllanthus urinaria*, wherein the polymersome comprises amphiphilic polymers having both hydrophobic and hydrophilic blocks, wherein the amphiphilic polymer is at least one selected from a hydroxyethyl acrylate/sodium acryloyldimethyl taurate copolymer, or an acrylate/stearyl methacrylate copolymer, and wherein the anti-aging peptide is diaminopropionoyl tripeptide-33.

2. The cosmetic composition for improving skin elasticity according to claim 1, wherein the peptide-enclosed polymersome, by percent of the total weight thereof, comprises 5% (w/w) to 15% (w/w) of the anti-aging peptide.

3. The cosmetic composition for improving skin elasticity according to claim 1, wherein the amphiphilic polymer consists of the hydroxyethyl acrylate/sodium acryloyldimethyl taurate copolymer and the acrylate/stearyl methacrylate copolymer.

4. The cosmetic composition for improving skin elasticity according to claim 1, wherein the composition increases production of a perlecan protein.

5. The cosmetic composition for improving skin elasticity according to claim 1, wherein the composition restores production of a perlecan protein decreased by UV.

6. The cosmetic composition for improving skin elasticity according to claim 1, wherein the composition improves skin wrinkles, restores skin elasticity and increases skin water content.

7. A method for improving skin elasticity comprising administering a composition comprising effective amounts of:
    *Phyllanthus urinaria* extract; and
    a polymersome in which one or more anti-aging peptide is enclosed, to a subject in need thereof,
    wherein the *Phyllanthus urinaria* extract is an ethanol extract of *Phyllanthus urinaria*, wherein the polymersome comprises amphiphilic polymers having both hydrophobic and hydrophilic blocks, wherein the amphiphilic polymer is at least one selected from a hydroxyethyl acrylate/sodium acryloyldimethyl taurate copolymer, or an acrylate/stearyl methacrylate copolymer, and wherein the anti-aging peptide is diaminopropionoyl tripeptide-33.

8. The method according to claim 7, wherein the peptide-enclosed polymersome, by percent of the total weight thereof, comprises 5-15 wt % of the anti-aging peptide.

9. The method according to claim 7, wherein the amphiphilic polymer consists of the hydroxyethyl acrylate/sodium acryloyldimethyl taurate copolymer and the acrylate/stearyl methacrylate copolymer.

10. The method according to claim 7, wherein the *Phyllanthus urinaria* extract and the polymersome increase production of a perlecan protein.

11. The method according to claim 7, wherein the *Phyllanthus urinaria* extract and the polymersome restore production of a perlecan protein decreased by UV.

12. The method according to claim 7, wherein the *Phyllanthus urinaria* extract and the polymersome improve skin wrinkles, restore skin elasticity and increase skin water content.

\* \* \* \* \*